United States Patent
Strohner et al.

(10) Patent No.: US 6,270,983 B1
(45) Date of Patent: Aug. 7, 2001

(54) SURFACES COATED WITH STREPTAVIDIN/AVIDIN

(75) Inventors: Pavel Strohner, Berlin; Ulrike Immer, Grävenwiesbach, both of (DE)

(73) Assignee: BioTeZ Berlin-Buch GmbH (DE)

( * ) Notice: Subject to any disclaimer, the term of this patent is extended or adjusted under 35 U.S.C. 154(b) by 0 days.

(21) Appl. No.: 09/424,960

(22) PCT Filed: Jun. 4, 1998

(86) PCT No.: PCT/DE98/01527

§ 371 Date: Feb. 22, 2000

§ 102(e) Date: Feb. 22, 2000

(87) PCT Pub. No.: WO98/55864

PCT Pub. Date: Dec. 10, 1998

(30) Foreign Application Priority Data

Jun. 6, 1997 (DE) .............................................. 197 24 787

(51) Int. Cl.⁷ ....................... G01N 33/53; G01N 33/543; G01N 15/06; B05D 3/10; C12M 1/40
(52) U.S. Cl. ........................... 435/7.5; 530/367; 530/810; 530/811; 530/812; 530/813; 530/814; 530/815; 530/816; 435/7.1; 435/7.92; 435/174; 435/287.1; 435/287.8; 435/287.9; 435/969; 436/174; 436/176; 436/178; 436/518; 436/524; 436/528; 436/532; 436/533; 422/57; 422/68.1; 427/207.1; 427/343; 428/403
(58) Field of Search ............................... 422/57, 68.1, 69, 422/70; 424/94.1, 1.11, 1.49, 9.1, 177.1, 178.1, 184.1, 287.1, 804, 809, 812; 428/407, 403; 427/207.1, 208, 343; 435/4, 5, 6, 7.1, 7.91, 7.92, 7.9, 7.93, 7.94, 7.95, 181, 188, 174, 176, 177, 180, 287.1, 287.2, 287.7, 287.9, 288.3, 803, 805, 810; 436/818, 819, 827, 523, 544, 519, 824, 529, 545, 537, 541, 514, 596, 546, 524, 532, 533, 807, 530, 534, 527, 528, 800, 810, 161, 172, 177, 178, 501, 518, 53, 536, 543, 547, 808; 530/810–816, 367

(56) References Cited

U.S. PATENT DOCUMENTS

| | | | |
|---|---|---|---|
| 4,228,237 | * 10/1980 | Hevey et al. | 435/7 |
| 4,282,287 | * 8/1981 | Giese | 428/407 |
| 4,496,654 | * 1/1985 | Katz et al. | 435/7 |
| 5,061,640 | * 10/1991 | Tischer et al. | 436/527 |
| 5,164,299 | * 11/1992 | Lambert | 435/7.92 |
| 5,212,063 | * 5/1993 | Ofenloch-Hahnle et al. | 435/7.5 |
| 5,252,743 | * 10/1993 | Barrett et al. | 548/303.7 |
| 5,268,306 | * 12/1993 | Berger et al. | 436/527 |
| 5,332,679 | * 7/1994 | Simons et al. | 436/518 |
| 5,362,624 | * 11/1994 | Schmitt et al. | 435/7.5 |
| 5,374,516 | * 12/1994 | Sutton et al. | 435/5 |
| 5,863,740 | * 1/1999 | Kientsch-Engel et al. | 435/7.5 |
| 5,986,076 | * 11/1999 | Rothschild et al. | 536/22.1 |

FOREIGN PATENT DOCUMENTS 0 529 775-A1 * 3/1993 (EP) .

OTHER PUBLICATIONS

Ebersole et al. Spontaneously formed functionally active avidin monolayers on metal surfaces: A strategy for immobilizing biological reagents and design of piezoelectric biosensors. J. Am. Chem. Soc. (1990) vol. 112, No. 8, pp. 3239–3241.*

Remy et al. Potentially of an organometallic labelled streptavidin–biotin system in metalloimmunoassay. Journal of Pharmaceutical and Biomedical Analysis. vol. 9, No. 10–12 (1991) pp. 965–967.*

Cordiano et al. Biotin–avidin immobilization of platelet glycoproteins (BAIPG): A new capture assay for the detection of anti–platelet antibodies. Journal of Immunological Methods. vol. 178, No. 1 (1995) pp. 121–130.*

Suter et al. The immunochemistry of sandwich ELISAs III: The Stoichiometry and efficacy of the protein–avidin–biotin capture (PABC) System. Molecular Immunology vol. 26, No. 3 (1989) pp. 221–230.*

Toru. Measuring method for antibody. Patent Abstracts of Japan. vol. 16, No. 586 (1992).*

Wood. A universal solid–phase assay system based on avidin–biotin reagents. Arztliche Laboratorium vol. 35, No. 2 (1989) pp. 29–34.*

G. Garrett et al.; Preparation of Oligonucleotide–Biotin Conjugates with Cleavable Linkers; Bioconjugate Chem. 1995, 6, pp. 135–138.

* cited by examiner

Primary Examiner—Long V. Le
Assistant Examiner—Kartic Padmanabhan
(74) Attorney, Agent, or Firm—Norris, McLaughlin & Marcus P.A.

(57) ABSTRACT

The invention relates to surfaces coated with streptavidin and avidin for use in immunoassays, wherein the surfaces comprise a layer of streptavidin and avidin which are bonded on a surface of a solid supporting material through a biotinylated adhering agent.

21 Claims, No Drawings

SURFACES COATED WITH STREPTAVIDIN/AVIDIN

BACKGROUND OF THE INVENTION

The invention relates to surfaces coated with streptavidin/avidin. Fields of application of the invention are medical diagnostics and pharmaceutical industry.

To determine immunologically effective components according to the principle of the solid phase immunoassay where a reactant is bonded on a solid phase today usually reaction vessels in the form of tubes or wells of microtitration plates are used as solid phase on the inner surfaces of which or outer surfaces of pellets the reactant is bonded. It is the aim to coat these surfaces with organic chemical substances in a way as to reach highly specific bonds in the subsequent assay and to keep the number of non-specific bonds as small as possible.

In the last few decades the immunoassay in its multifarious forms has become established for the determination of a specific bondable immunological substance. It is possible to determine smallest substance quantities in the presence of a billionfold excess of foreign matter. The basis is the sensitive and specific competitive reaction of a non-marked substance P with a fixed quantity of a marked substance P* around specific bonding sites of a binding agent Q in a limited quantity. The concentration of the latter may be determined from the distribution pattern of the marked ligand as a function of the concentration of non-marked ligands. Various methods for separating converted from non-converted reactants have been developed.

In the last few years the solid phase method where one reactant is bonded on a solid phase gained major importance. Reactants bonded chemically or physically on the solid phase may be antibodies, antigens, receptors, cells, DNA, RNA etc. These reactants may be adsorbed on the solid phase either directly or through a precoating. Today it is usually modified with a specifically bondable substance, biotin, which allows to bond it on the coated supporting material (Patent DE 36 40 412 A1 and: Soukup, G. A. et al.: Bioconjugate Chemistry 6, 135/1995).

Today usually plastic surfaces of polystyrene, polypropylene, polyethylene, polyamide, polymethacrylate, polycarbonate, polyacrylate or copolymeres of polystyrene are used as supporting material in the form of inner surfaces of tubes or wells of microtitration plates or outer surfaces of pellets.

Various modifications of these surfaces are known. Thereby, the specifically bonding substance shall be bonded in a way as to make the bondage of the reactant modified by biotin stable, unaffected and sufficient for all manipulations required during the determination procedure. Here, the modified, specifically bonding reactant shall not lose its bondability. Today most of the coatings of solid phases are based on adsorptive bonds.

To ensure stability and an optimum coating adhering agents bringing about an adsorptive bonding were recommended. Here, there shall be made sure that the bondability of the specifically bonding reactant will not be affected (Patent DE 38 06 431).

The determination procedures so far known show the following drawbacks:
  the adsorptive loading with reactants frequently results in a too low loading,
  a too low absorbancy of the coated surfaces for bonding the reactants subsequently biotinylated,
  high non-specific bonding occurring frequently,
  instability towards aggressive substances such as detergents, strong bases or acids.

SUMMARY OF THE INVENTION

Proceeding on this the invention was aimed at developing a coated solid phase which provides high surface bonding yields and a sufficient stability, also in the presence of detergents, which is universally applicable, thus facilitating the required sensitivity of the determination procedure to be conducted.

The aim of the invention is reached according to patent claims 1 and 17, the sub-claims are preferential variants.

The supporting material is in a first stage adsorptively loaded with a hydrophobic adhering agent which, on its turn, is modified by a specific bonding agent for a further, specifically bonding substance. The adhering agent may be a polypeptide, protein, carbohydrate or glycoprotein. It may be used non-cross-linked, cross-linked or derivatized. Proteins with a molecular weight between 10 000 and 900 000 are used preferably for hydrophobing and/or cross-linkage. RSA, lipase or immune globulins such as immune globulin gamma, are especially preferred. The adhering agent has to be more hydrophobic than the supporting material.

DETAILED DESCRIPTION OF THE INVENTION

According to the invention the adhering agent is modified by a bonding agent, the biotin. This is used to produce a stable bond with a further specifically bondable substance, the streptavidin and/or avidin, which results in a stably coated solid phase of a new quality according to the invention. Streptavidin and/or avidin have a few bonding sites for biotin, being thus able to subsequently bond with reactants of a determination procedure modified by biotin. Thereby, on the one hand, the strong biotin-streptativin and/or avidin bond and on the other hand, the fact that streptavidin or avidin have four bonding sites for biotin are taken advantage of. To our surprise, the coated surfaces have the ability that the remaining bonding vacancies for biotin react with a greater affinity with the reactants modified by biotin to be bonded subsequently in spite of the fact that bonding sites were taken by streptavidin and/or avidin due to being bonded on the biotinylated adhering agent. This leads to an extremely stable and highly sensitive solid phase allowing to make the determination procedures developed on this solid phase by far more sensitive. This becomes apparent notably when detecting biotinylated oligonucleotides and DNA fragments where smallest quantities may be detected. The coated solid phase applied according to the invention is able to react sensitively to smallest differences.

The adhering protein may be used non-cross-linked as an individual molecule, cross-linked or derivatized. The methods of preparation are known to the specialist, equally the method of biotinylation. Harmonizing of the degree of cross-linkage with the degree of biotinylation, the choice of the respective adhering agent, the quantity of the adhering agent and of streptavidin and/or avidin with each other and with the biotinylated adhering substance is essential to the implementation of the invention. Immune globulin gamma is an especially preferred form as adhering agent. It may be applied non-cross-linked as well as preferably cross-linked with the known spacers.

As a general rule, there applies the higher the degree of cross-linkage and biotinylation the less adhering protein has to be used. It is important that not too many biotin bonding sites on streptavidin and/or avidin will be occupied, otherwise the effect will be reversed. The streptavidin/avidin quantity has to be harmonized with the quantity of the biotinylated adhering protein.

TABLE

Cross-linkage agents used

| short form | chemical designation |
|---|---|
| SPDP | N-succinimidyl-3-(2-pyridylditho)-propionate |
| DSS | disuccinimidyl suberate |
| DMS | dimethyl suberimidate |
| MHS | malimidohexanoyl-n-hydroxysuccinimide ester |
| MABI | methyl-4-azidobenzoimidate * HCl |
| SAMBA | S'-acetyl-mercapto succinoanhydride |
| MBS | m-maleinimidobenzoyl-n-hydroxysuccinimide ester |
| SATP | n-succinimidyl-S-acetyl thiopropionate |
| SATA | n-succinimidyl-s-acetylthioacetate |
| SADP | n-succinimidyl-(4-azidophenyl)-1,3'-dithiopropionate |

After cross-linkage preferably immune globulin gamma is biotinylated according to the usual methods.

TABLE

Biotinylation reagents used

| NHS-biotin | biotin hydrazide |
|---|---|
| NHS-LC-biotin | biotin LC-hydrazide |
| sulpho-NHS-LC-biotin | biotinamido pentylamine |
| NHS-SS-biotin | |

According to the invention the degree of biotinylation is in the range between 10 and 35. The quantities of cross-linked, biotinylated adhering protein used are between 5 and 15 μg/ml of coating solution depending on the degree of biotinylation.

Hereinafter the biotin-streptavidin and/or avidin bonding is carried out on the solid phase. The quantities are between 2.5 and 20 μg/ml depending of the preloading with the adhering protein. Subsequently, the solid phase is stabilized according to methods known to the specialist. It may be now stored for a few months, is universally applicable for all determination procedures where a reactant was modified by biotin. The coated solid phase is constituted in a way as to be used for all procedures known. In a special form of execution the solid phase is constituted in a way (well of microtiration plates) that it serves, at the same time, as a photometric cuvette. Thus, the measurement of the substance to be determined may be carried out at the surface in the same vessel upon termination of the reaction.

The method results in high signal yields on the coated solid phase, with the non-specific bonds being minimized. The solid phase is stable to effects of detergents. That is why the developed solid phase may be used preferably in such determination procedures where this plays a special part. It is excellently suited for RNA and DNA diagnostics, with streptavidin/avidin mixtures being especially preferred for this.

The invention will be explained in greater detail hereinafter by means of examples of execution.

EXAMPLES OF EXECUTION

Example 1

Thyreoglobulin-ELISA (TG-ELISA) on the Coated Solid Phase

TG-ELISA is an enzyme immunometric assay consisting of a biotinylated catcher antibody (monoclonal), a TG-standard and a POD-marked signal antibody (monoclonal). The separation is effected on the coated solid phase described (wells of microtitration plates (MTP). Both antibodies are bonded on various bonding domains of TG. Thus TG forms a specific bridge between the two antibodies (sandwich).

Description

Two hundred microlitres of a biotinylated immune globulin gamma (hulgG) solution cross-linked with DSS in a 0.1 m carbonate buffer, pH 9.6, (cross-linked with a 20-fold excess of DSS and biotinylated with a degree of biotinylation of 15) are put into the wells of a MTP for 30 minutes. After having been washed twice with 0.9% NaCl the wells incubate in a second stage with two hundred microlitres of a solution consisting of 10 μg of streptavidin and 10 μg of avidin per millilitre of a 0.1 m carbonate buffer, pH 9.6. After four hours it is 2 times washed with 0.9% NaCl, after-blocked with 0.1% casein for 30 min. and blocked with a 5% Denhart's solution in a 0.1 m Mc Ilvaine buffer (pH 6) (0.05% RSA) for further 30 minutes. Finally it is sucked off and the MTP are dried overnight. The plates thus coated are welded in foil with a drying agent and stored at 4° C. up to being used. The MTP is loaded with 200 μl of a biotylinated catcher antibody overnight for the TG assay and subsequently blocked with 0.2% milk powder for 30 min. For carrying out the assay 100 μl of Mc Ilvaine buffer, pH 6 (0.5% of RSA), 50 μl of TG standard in a dilution series or 50 μl of sample of an unknown concentration and 50 μl of signal antibody POD are allowed to react with the antibodies bonded on the solid phase. After 4 h the converted complex and the unconverted reactants are separated by sucking off. TG is bonded on the surface in a quantity which is available in the solution. The signal antibody POD recognizes the bonded TG quantity. Through a topped substrate POD (horse radish peroxidase enzyme) reaction the bonded TG quantity may be determined. O-phenylene diamine (OPD) is used as substrate. The level of the signal is proportionate to the quantity of the available TG. Unknown samples are determined by means of their signal level from a calibration curve.

Example 2

Hybridization of Two Oligonucleotides of a Complementary Structure on the Coated Surface (Artificial System)

Two hundred microlitres of a biotinylated immune globulin gamma (hulgG) solution cross-linked with DSS in a 0.1 m carbonate buffer, pH 9.6, (cross-linked with a 20-fold excess of DSS and biotinylated with a degree of biotinylation of 15) are put into the wells of a MTP for 30 min. After having been washed with 0.9% NaCl two times the wells incubate in a second stage with two hundred microlitres of a solution of 10 μg of streptavidin and 10 μg of avidin per millilitre 0.1 m carbonate buffer, pH 9.6. After four hours it is washed with 0.9% NaCl two times, afterblocked with 0.1% casein for 30 min. and blocked with a 5% Denhart's solution in a 0.1 m Mc Ilvaine buffer, pH 6 (0.05% of RSA). Finally it is sucked off and the MTP are dried overnight. The plates thus coated are welded in foil with a drying agent and stored at 4° C. until being used. 50 μl of a biotinylated oligonucleotide single strand (80 mer) of a rising concentration are applied onto a coated MTP for 30 min. at 37° C. Subsequently, it is washed once with 0.9% of NaCl Tween (0.1%) and hybridized with 50 μl of a FITC-marked signal strand (18 mer). Thereupon it is anew washed with 0.9% NaCl Tween (0.1%). For detecting hybridization 100 μl of a mixture of anti-FITC antibodies (monoclonal) and a second anti-mouse antibody POD is added in equal portions for 15 min. Thereupon the enzyme-substrate reaction is effected with 50 µl of TMB solution (tetramethyl benzidine). Unknown concentrations of a biotinylated sample may be read off from the calibration curve with rising quantities of the biotinylated single strand by the level of the measured signal.

What is claimed is:

1. Surfaces coated with streptavidin and avidin comprising a layer of streptavidin and avidin which is directly bonded to a surface of a solid supporting material through a biotinylated adhering agent.

2. The surfaces coated with streptavidin and avidin according to claim 1 wherein the adhering agent is cross-linked or not cross-linked.

3. The surfaces coated with streptavidin and avidin according to claim 1 wherein the adhering agent is derivatized.

4. The surfaces coated with streptavidin and avidin according to claim 1, wherein the adhering agent is at least 10 kDa and is selected from the group consisting of polypeptides, carbohydrates, proteins, and glycoproteins.

5. The surfaces coated with streptavidin and avidin according to claim 1, wherein the adhering agent is selected from the group consisting of RSA, lipase, and immune globulin.

6. The surfaces coated with streptavidin and avidin according to claim 1, wherein the adhering agent is immune globulin gamma.

7. The surfaces coated with streptavidin and avidin according to claim 1, wherein the adhering agent is cross-linked to a degree of between 10 and 30 moles of a cross-linking agent.

8. The surfaces coated with streptavidin and avidin according to claim 1, wherein the adhering agent is biotinylated to a degree of between 15 and 35 moles of a biotinylating agent.

9. The surfaces coated with streptavidin and avidin according to claim 1, wherein the adhering agent is used in coating solutions of a concentration between 5 and 15 µg/ml.

10. The surfaces coated with streptavidin and avidin according to claim 1, wherein loading with streptavidin and avidin is effected by means of coating solutions of a concentration between 5 and 20 µg/ml.

11. The surfaces coated with streptavidin and avidin according to claim 1, wherein streptavidin and avidin are used in a ratio between 60:40 to 40:60.

12. The surfaces coated with streptavidin and avidin according to claim 11, wherein a streptavidin and avidin are used in a ratio of 50:50.

13. The surfaces coated with streptavidin and avidin according to claim 1, wherein the adhering agent is non-crosslinked with a degree of biotinylation of 35 and 5–10 µg/ml of the adhering agent is used.

14. The surfaces coated with streptavidin and avidin according to claim 1, wherein the adhering agent is cross-linked by a cross-linking agent, the adhering agent having a degree of biotinylation of 15–20 and being present in an amount of 10 µg/ml.

15. The surfaces coated with streptavidin and avidin according to claim 1, wherein the adhering agent is adsorptively bonded on the surface.

16. The surfaces coated with streptavidin and avidin according to claim 1, wherein the adhering agent is bonded on the wells of microtitration plates.

17. A method of preparing surfaces coated with streptavidin and avidin comprising applying the biotinylated adhering agent onto the surface and, after its adsorption, the layer comprising streptavidin and avidin is applied in a second stage, wherein the layer of avidin and streptavidin binds directly to the biotinylated adhering agent.

18. The surfaces coated with streptavidin and avidin according to claim 14, wherein the cross-linking agent is a 10–30 fold excess of disuccinimidyl substrate.

19. The surfaces coated with streptavidin and avidin according to claim 1, wherein the solid supporting material is selected from the group consisting of inner surfaces of tubes, wells of microtitration plates, and outer surfaces of pellets.

20. The surfaces coated with streptavidin and avidin according to claim 19, wherein the solid supporting material is made from one or more of the following chosen from the group consisting of polystyrene, polypropylene, polyethylene, polyamide, polymethacrylate, polycarbonate, polyacrylate, and copolymers of polystyrene.

21. The surfaces coated with streptavidin and avidin according to claim 8, wherein the biotinylating agent is selected from the group consisting of NHS-biotin, NHS-LC-biotin, sulpho-NHS-LC-biotin, NHS-SS-biotin, biotin hydrazide, biotin LC-hydrazide, and biotinamido pentylamine.

* * * * *